(12) United States Patent
Yoon et al.

(10) Patent No.: US 9,683,012 B2
(45) Date of Patent: Jun. 20, 2017

(54) METHOD OF ANTIBODY PURIFICATION

(71) Applicant: PRESTIGE BIOPHARMA PTE. LTD., Singapore (SG)

(72) Inventors: Ji Yong Yoon, Yuseong-gu (KR); Dong Eun Lee, Yuseong-gu (KR); Won Kyum Kim, Yuseong-gu (KR); Jeong Won Youn, Sejong (KR); Jung Eun Baek, Daejeon (KR)

(73) Assignee: PRESTIGE BIOPHARMA PTE. LTD., Singapore (SG)

(*) Notice: Subject to any disclaimer, the term of this patent is extended or adjusted under 35 U.S.C. 154(b) by 202 days.

(21) Appl. No.: 14/365,027

(22) PCT Filed: Dec. 14, 2012

(86) PCT No.: PCT/KR2012/010899
§ 371 (c)(1),
(2) Date: Jun. 12, 2014

(87) PCT Pub. No.: WO2013/089477
PCT Pub. Date: Jun. 20, 2013

(65) Prior Publication Data
US 2014/0316115 A1 Oct. 23, 2014

(30) Foreign Application Priority Data
Dec. 15, 2011 (KR) .................. 10-2011-0135652

(51) Int. Cl.
C07K 1/20 (2006.01)
C07K 1/18 (2006.01)
C07K 1/36 (2006.01)
C07K 16/06 (2006.01)
C07K 16/32 (2006.01)

(52) U.S. Cl.
CPC .............. *C07K 1/20* (2013.01); *C07K 1/18* (2013.01); *C07K 1/36* (2013.01); *C07K 16/065* (2013.01); *C07K 16/32* (2013.01)

(58) Field of Classification Search
None
See application file for complete search history.

(56) References Cited

U.S. PATENT DOCUMENTS

| | | | |
|---|---|---|---|
| 9,102,723 B2 | 8/2015 | Wan et al. | |
| 2003/0059862 A1* | 3/2003 | Ruben ................ | C07K 16/2875 435/7.23 |
| 2006/0030696 A1* | 2/2006 | Bonnerjea ............... | C07K 1/22 530/387.1 |
| 2007/0029244 A1 | 2/2007 | Wnuk et al. | |
| 2012/0177640 A1* | 7/2012 | Burg ...................... | C07K 1/18 424/133.1 |
| 2012/0202974 A1 | 8/2012 | Eon-Duval et al. | |
| 2014/0288278 A1* | 9/2014 | Nti-gyabaah ......... | B01D 15/3809 530/388.24 |

FOREIGN PATENT DOCUMENTS

| | | |
|---|---|---|
| JP | 2009-532474 A | 9/2009 |
| JP | 2010-516651 A | 5/2010 |
| KR | 10-2007-0001968 A | 1/2007 |
| KR | 10-2009-0005315 A | 1/2009 |
| WO | 2007/117490 A2 | 10/2007 |
| WO | 2008/087184 A2 | 7/2008 |
| WO | WO 2009058769 A1 * | 5/2009 ............... C07K 1/18 |
| WO | 20111009623 A1 | 1/2011 |
| WO | 2011/098526 A1 | 8/2011 |

OTHER PUBLICATIONS

"Fractogel Chromatography Resin: Caputre your target with speed and efficiency" copyright 2014 EMD Millipore Corporation, obtained from www.emdmillipore.com/Fractogel, pp. 1-12.*
GE Healthcare Life Sciences "Phenyl Sepharose 6 Fast Flow (High Sub), 1 1", p. 1, obtained from the internet at http://www.gelifesciences.com/webapp/wcs/stores/servlet/productByld/en/GELifeSciences-us/17097303.*
Extended European Search Report issued on Jul. 16, 2015 in EP Application No. 12857495.1 (PCT/KR2012/010899), total 7 pages.
Notification of Preliminary Rejection issued on Sep. 7, 2015 in JP Application No. 2014-547103, total 9 pages with English translation.
The State Intellectual Property Office of the People's Republic of China, Notice of the First Office Action issued on Jul. 28, 2015 in CN Application No. 2012800609396, total 10 pages with English translation.
Pete Gagnon, "Use of Hydrophobic Interaction Chromatography With a Non-Salt Buffer System for Improving Process Economics in Purification of Monoclonal Antibodies", TOSOH Bioscience BMBH, Miami, Florida USA, Apr. 30-May 3, 2000.
Andreas Stein & Andre Kiesewetter, "Cation exchange chromatography in antibody purification: pH screening for optimaised binding and HCP removal", ScienceDirect, Journal of Chromatography B, vol. 848, pp. 151-158, Available online Nov. 17, 2006 at www.sciencedirect.com.
Deborah K. Follman & Robert I. Fahrner, "Factorial screening of antibody purification processes using three chromatography steps without protein A", ScienceDirect, Journal of Chromatography A, vol. 1024, pp. 79-85, Available online at www.sciencedirect.com.
Sven Sommerfeld & Jochen Strube, "Challenges in biotechnology production—generic processes and process optimization for monoclonal antibodies", ScienceDirect, Chemical Engineering and Processing Vo.44, pp. 1123-1137, Available online May 23, 2005 at www.sciencedirect.com.
Warren Schwartz, David Judd, Michelle Wysocki, Luc Guerrier, Eszter Birck-Wilson & Egisto Boschetti, "Comparison of hydrophonic charge induction chromatography with affinity chromatography on protein A for harvest and purification of antibodies", Journal of Chromatography A. vol. 908, pp. 251-263, www.elsevier.com/locate/chroma.
Egisto Boschetti, "The use of thiophilic chromatography for antibody purification: a review", Journal of Biochemical and Biophysical Methods, vol. 49, pp. 361-389, www.elsevier.com/locate/jbbm.
Hongcheng Liu, Georgeen Gaza-Bulseco & Joanne Sun, "Characterization of the stability of a fully human monoclonal IgG after prolonged incubation at elevated temperature", Journal of Chromatography B, vol. 837, pp. 35-43, Available online Apr. 27, 2006 at www.sciencedirect.com.

(Continued)

*Primary Examiner* — Daniel E Kolker
*Assistant Examiner* — James Rogers
(74) *Attorney, Agent, or Firm* — Masuvalley & Partners

(57) ABSTRACT

The present invention relates to a method for preparing a population of antibodies to have high purity and high quality by removing antibody isoforms and impurities through the use of a cation exchange column, a hydrophobic interaction column, and an anion exchange column successively, without using a protein A column; and to a population of antibodies prepared by the above method.

18 Claims, 9 Drawing Sheets

(56) References Cited

OTHER PUBLICATIONS

Isam Terashima, Akiko Koga & Hiroshi Nagai, "Identification of deamidation and isomerization sites on pharmaceutical recombinant antibody using H2 18O", Analytical Biochemistry vol. 368, pp. 49-60, Available online May 17, 2007 at www.sciencedirect.com.

Reed J. Harris, Bruce Kabakoff, Frank D. Macchi, Felicity J. Shen, May Kwong, James D. Andya, Steven J. Shire, Nancy Bjork, Klara Totpal & Anthony B. Chen, "Identification of multiple sources of charge heterogeneity in a recombinant antibody", Journal of Chromatography B, vol. 752, pp. 233-245, www.elsevier.com/locate/chromb.

Boxu Yan, Sean Steen, David Hambly, John Valliere-Douglass, Tim Vanden Bos, Scott Smallwood, Zac Yates, Thomal Arroll, Yihong Han, Himanshu Gadgil, Ramil F. Latypov, Alison Wallace, Aiching Lim, Gerd R. Kleemann, Weichun Wang & Alain Balland, "Succinimide Formation at Asn 55 in the Complementarity Determining Region of a Recombinant Monoclonal Antibody IgG1 Heavy Chain", Journal of Pharmaceutical Sciences, vol. 98, No. 10, pp. 3509-3521, Oct. 2009.

Chris Chumsae, Georgeen Gaza-Bulseco, Joanne Sun & Hongcheng Liu, "Comparison of methionine oxidation in thermal stability and chemically stressed samples of a fully human monoclonal antibody", Journal of Chromatography B, vol. 850, pp. 285-294, Available Dec. 19, 2006 at www.sciencedirect.com.

William E. Werner, Sylvia Wu & Michael Mulkerrin, "The removal of pyroglutamic acid from monoclonal antibodies without denaturation of the protein chains", Analytical Biochemistry Vo.342, pp. 120-125, Available online Apr. 27, 2005 at www.sciencedirect.com.

\* cited by examiner

Fig. 10
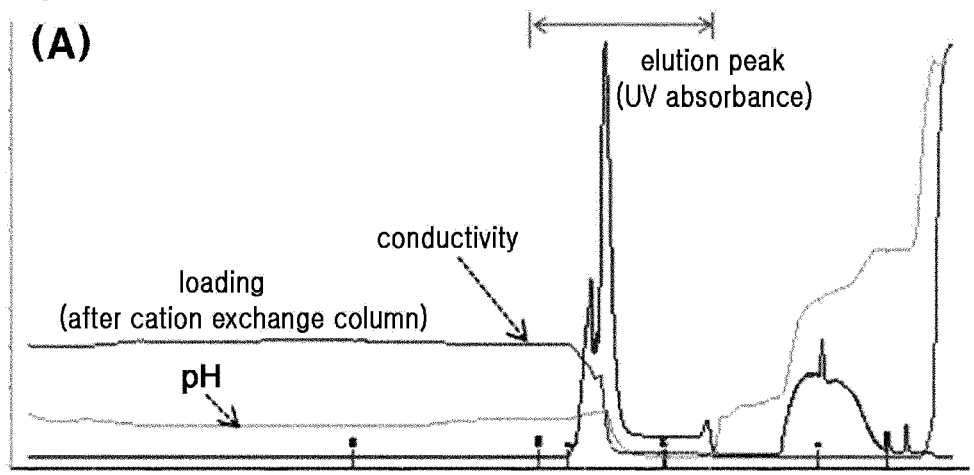
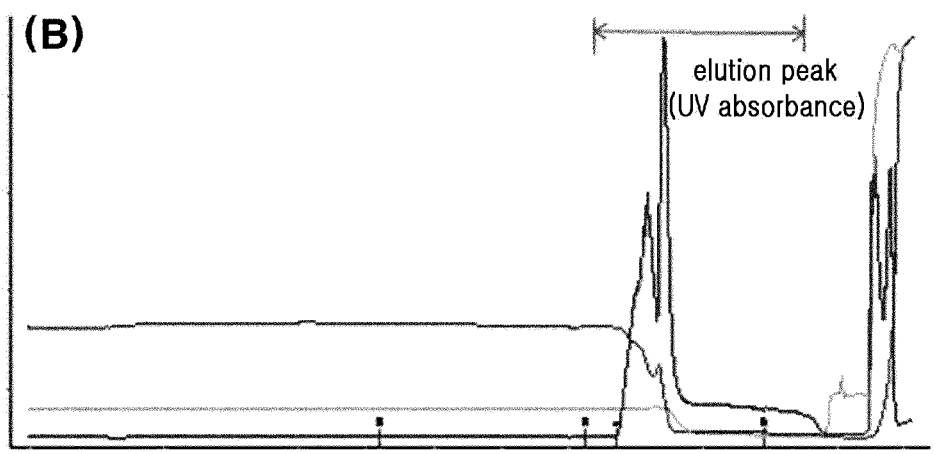
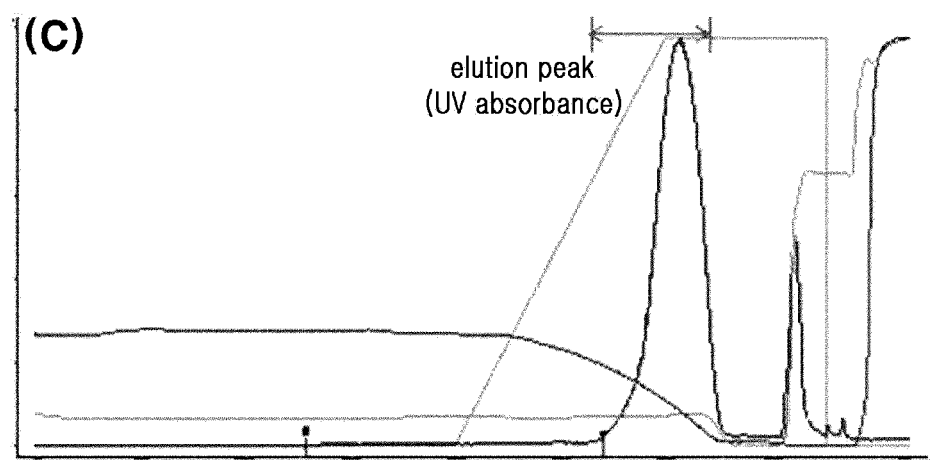

METHOD OF ANTIBODY PURIFICATION

TECHNICAL FIELD

The present invention relates to a method for preparing a population of antibodies to have high purity and high quality by removing antibody isoforms and impurities through the use of a cation exchange column, a hydrophobic interaction column, and an anion exchange column successively, without using a protein A column; and to a population of antibodies prepared by the above method.

BACKGROUND ART

A Protein A column is commonly used in many of the purification processes used for the production of antibody drugs. The use of Protein A column has the advantage of having production with high purity at the early stage of the process. However, the cost of Protein A is 30 times more expensive than that of other commonly-used ion exchange resins, resulting in a high production costs for antibody drugs.

According to previous reports, the Protein A resin accounts for about 35% of the raw material costs associated with antibody drug production (Journal of Chromatography A, 1024 (2004) 79-85), and trace amounts of Protein A remaining in the antibody sample may cause immunogenic or other physiological responses when administered to humans (Purification Tools for Monoclonal Antibodies, Validated Biosystems, Tucson, Ariz., 1996). Therefore, purification processes using Protein A column require constant monitoring and removal of residual Protein A in each purification step. In addition, since Protein A works based on its bioaffinity towards the target, it has the disadvantage of low chemical stability. Thus, to maintain the bioactivity of Protein A, 1 M NaOH cannot be used even though it is essential for cleaning the column to make it available for subsequent use. Without using 1 M NaOH, it is hard to completely remove impurities from the column, and thus the number of times that the column can be re-used is substantially lower than the number allowed by the use of chemical resins.

Despite the high cost, major global pharmaceutical companies prefer using Protein A for purification of antibodies because it can achieve high purity of antibodies at the early stage. For instance, Genentech produces an antibody drug, namely Herceptin which is purified through a process utilizing Protein A, a cation exchange resin, an anion exchange resin, and a hydrophobic interaction resin (HIC) (Sven Sommerfeld a, Jochen Strube b, Chemical Engineering and Processing 44 (2005) 1123-1137). However, due to the disadvantages of Protein A described above, a more efficient and cost-effective purification method for antibodies still needs to be developed.

In order to develop an antibody purification method that does not use Protein A column, the first requirement for any alternative method is that it removes impurities to an equal or greater than Protein A. Especially when a CHO cell line is used as a host cell for producing the antibody, the cell culture contains not only the desired antibodies, but also a large amount of impurities including host cell proteins (HCPs), host cell-derived DNAs (HCDs), and growth factors. Therefore, in any case not using Protein A for antibody purification, successful removal of impurities at the early stage is an important factor due to the high amount of impurities.

To solve this problem, Warren Schwartza et al. have developed an antibody purification method that uses MEP HyperCel which is a type of hydrophobic charge induction chromatography (HCIC) (Journal of Chromatography A, 908 (2001) 251-263). In this method, antibodies having high purity are isolated without ultrafiltration from the cell culture containing salts. However, HCIC is still 2 to 5 times more expensive than the use of ion exchange resins. Also it has not been found whether the removal of impurities through HCIC is more effective than using ion exchange resins. Meanwhile, Egisto Boschetti has proposed using a thiophilic chromatography (T-gel) that is based on the chemical affinity of resin for producing an antibody having high purity, whereas Protein A chromatography is based on its own bioaffinity (J. Biochem. Biophys. Methods 49 (2001) 361-389). However, T-gel is still not as effective as Protein A for preparing antibodies having high purity and also its cost is 5 times higher than that of the method using ion exchange resins. Therefore it has not been used in the industry as of yet.

Meanwhile, as another purification method, an ion exchange resin such as a cation exchange resin can be used in an adsorption column. Examples of cation exchange resins that are currently used in the industry include CM Fast Flow and SP Fast flow manufactured from GE-healthcare, and Fractogel $SO_3$ and Fractogel $COO^-$ manufactured from Merck (US2007029244). However, a cation exchange resin still has the limitation of inefficient removal of impurities at the early stage. Likewise, optimizing the numerous conditions of the purification process is the key for a successful development of a novel purification process.

In the antibody purification process, maintaining the consistency of quality is as important as the removal of impurities. An antibody consists of two heavy chains and two light chains which are linked by disulfide bonds, while the Fc portion of the heavy chain is glycosylated. However, the antibodies produced in CHO cells used as a host cell include various isoforms (Hongcheng Liu, Georgeen Gaza-Bulseco, Journal of Chromatography B, 837 (2006) 35-43). Most of the isoforms have few amino acid modification such as deamidation, oxidation, and the like (Isamu Terashima, Akiko Koga, Analytical Biochemistry 368 (2007) 49-60). Especially, if the complementarity determining region (CDR) being antigen-binding site, is modified by deamidation thereby forming antibody isoforms, there is a reduction in the binding affinity of antigen to antibody, thereby affecting the bioactivity of the antibody (Reed J. Harrisa, Bruce Kabakoff, Journal of Chromatography B, 752 (2001) 233-245).

Various types of antibody isoforms can be formed, for example, by deamidation of asparagine yielding aspartate (Boxu Yan, Sean Steen, Journal of Pharmaceutical Sciences, Vol. 98, No. 10, October 2009), and by oxidation of methionine yielding methionine sulfate (Chris Chumsae, Georgeen Gaza-Bulseco, Journal of Chromatography B, 850 (2007) 285-294). In addition, glutamate at the N-terminal of heavy chains may be transformed into pyroglutamate by forming a five-member ring structure (William E. Werner, Sylvia Wu, Analytical Biochemistry 342 (2005) 120-125). Since these isoforms affect the bioactivity of antibodies, the proportion of isoforms present in the antibody needs to be controlled during the antibody production process.

For regulating the amount of antibody isoforms, a cation exchange chromatography can be used since it can isolate the desired antibodies adsorbed to the column by desorbing them based on the difference in net charge but an appropriate purification condition needs to be specified as well.

DISCLOSURE OF INVENTION

Technical Problem

In an effort to develop a method for preparing a population of antibodies with high quality and high purity without using a costly Protein A column, the inventors have developed the present invention, wherein the supernatant of the cell culture excluding cells is pre-treated by reducing pH for removing precipitates. Then the pre-treated sample is run through a cation exchange column, a hydrophobic interaction column, and an anion exchange column successively in order to remove the impurities such as host cell proteins (HCP) effectively, and ultimately to prepare a high quality population of antibodies with desired ratio of active antibodies and antibody isoforms.

Solution to Problem

It is an object of the present invention to provide a method for preparing a population of antibodies wherein over 65% of the population are active antibodies, comprising: (a) loading a sample comprising a mixture of antibodies to a pre-equilibrated cation exchange column, then optionally washing the column with an wash buffer, and eluting antibodies bound to the column with an elution buffer, thereby removing host cell proteins (HCPs) and antibody isoforms from the sample; (b) loading a sample prepared by mixing salt with the eluate of step (a) to a hydrophobic interaction column (HIC), and eluting the antibodies bound to the column with an elution buffer, thereby removing the host cell proteins (HCPs) from the eluate of step (a); and (c) loading the eluate of step (b) to an anion exchange column and collecting the flow-through.

It is another object of the present invention to provide a population of antibodies prepared by the above method, wherein more than 65% of the population are active antibodies.

Advantageous Effects of Invention

By using the preparation method of the present invention, the impurities can be effectively removed from the antibody-producing cell culture without using an expensive Protein A column, thereby producing a desired population of antibodies with high purity and quality.

BRIEF DESCRIPTION OF DRAWINGS

FIG. 10 shows a graph of AKTA process showing the effects of the different buffer conditions in hydrophobic interaction chromatography column ((A) buffer pH 7.2, stepwise elution, (B) buffer pH 6.0, stepwise elution, (C) buffer pH 6.0, concentration-gradient elution);

BEST MODE FOR CARRYING OUT THE INVENTION

Figure 1:
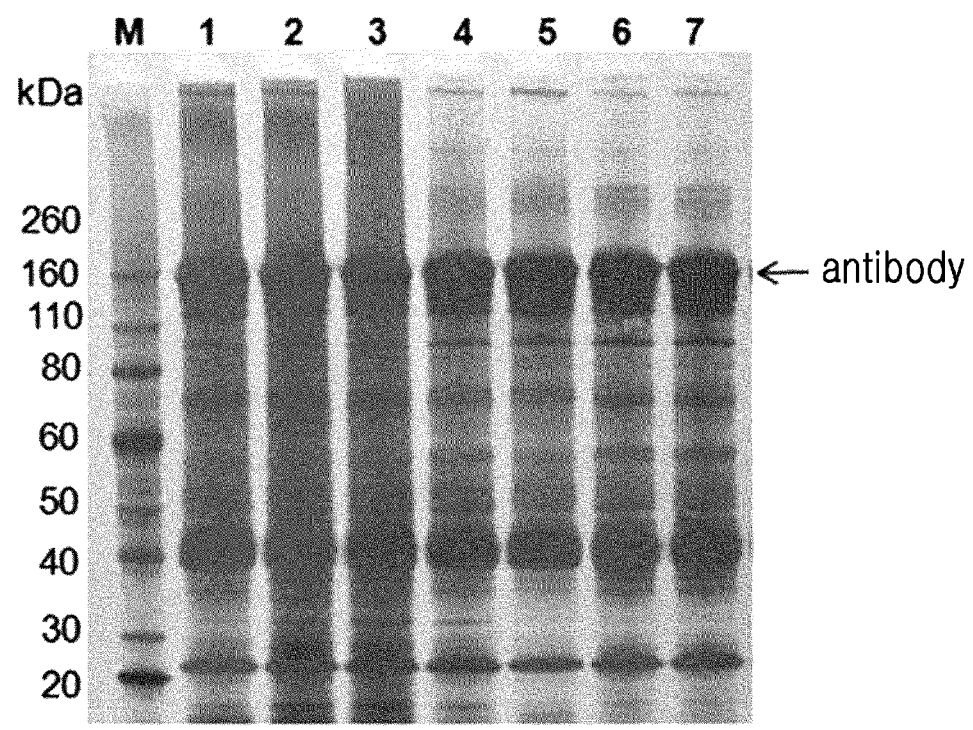
FIG. 1 shows the result of SDS-PAGE after removing impurities in the culture medium at pH 5, in which M: Protein size Marker, 1: culture medium, 2: depth filtering (after removal of cells) (Method 1), 3: after pH reduction to pH 5 and 1-hr low-speed stirring (Method 1), 4: after depth and sterile filtering (Method 1), 5: supernatant after pH reduction to pH 5 and 1-hr low-speed stirring (Method 2), 6: after depth filtering (Method 2), 7: after sterile filtering (Method 2)

As one aspect, the present invention provides a method for preparing a population of antibodies wherein over 65% of the population are active antibodies, comprising: (a) loading a sample comprising a mixture of antibodies to a pre-equilibrated cation exchange column, then optionally washing the column with an wash buffer, and eluting antibodies bound to the column with an elution buffer, thereby removing host cell proteins (HCPs) and antibody isoforms from the sample; (b) loading a sample prepared by mixing salt with the eluate of step (a) to a hydrophobic interaction column (HIC), and eluting the antibodies bound to the column with an elution buffer, thereby removing the host cell proteins (HCPs) from the eluate of step (a); and (c) loading the eluate of step (b) to an anion exchange column and collecting the flow-through.

The antibody products produced by the host cell contain not only the active antibodies but also various antibody isoforms, host cell proteins, DNA derived from the host cell, and growth factors of the cell. The antibody isoforms are the modified forms of antibody by deamidation or oxidation of certain amino acids, and these isoforms have different bioactivities. Antibody products expressed in the host cell contain a high portion of antibody isoforms. Especially when antibody biosimilars are manufactured, it is important to produce antibodies with high quality as a reference drug. Therefore, after producing antibodies in the host cells, a purification process is essential to control the amount of antibody isoforms in the antibody product.

In this regard, the present invention provides a method for preparing a population of antibodies which comprises desired proportions of acidic antibody isoforms, active antibodies, and basic antibody isoforms, by removing host cell proteins to increase the purity of antibodies and increasing a proportion of active antibodies compared to that in the initial culture supernatant.

As used herein, the term "a population of antibodies" refers to a group of antibodies including active antibodies and antibody isoforms. For the purpose of the present invention, the population of antibodies refers to a group of antibodies comprising a desired ratio of active antibodies and antibody isoforms. The group of antibodies may comprise only one type of antibody or both of active antibodies and antibody isoforms. For the purpose of the present invention, the population of antibodies may preferably refer to a group, wherein a proportion of active antibodies is increased by removing antibody isoforms and impurities such as host cell proteins from the culture supernatant.

In particular, when the method of the present invention is used to prepare antibody biosimilars, the population of antibodies refers to a group comprising active antibodies and antibody isoforms in the ratio that is the same as or corresponding to a reference drug.

Through a purification process using cation exchange column, the desired population of antibodies can be prepared comprising a desired ratio of antibody isoforms and active antibodies, preferably a proportion of active antibodies exceeding 65%, more preferably a proportion of basic antibody isoforms below 20%. Specifically, the population of antibodies may comprise 65 to 80% of active antibodies, 15 to 30% of acidic antibody isoforms, and 5 to 20% of basic antibody isoforms, but not is limited thereto. In one example of the present invention, a population of antibodies was prepared by using Fractogel COO⁻ cation exchange column to comprise 23.8% acidic antibody isoforms, 68.7% active antibodies and 7.5% basic antibody isoforms, which is similar to the proportions in the reference drug, namely Herceptin® (Example 2 and Table 7).

As used herein, the term "antibody" is a substance that is produced in the immune system by an antigen stimulation, and it binds to a specific antigen to induce antigen-antibody reaction while circulating in the lymph and blood. For the purpose of the present invention, the antibody is the target protein to be purified with a high quality, and it can be efficiently purified by the method of the present invention.

Because the antibody has a higher isoelectric point than other proteins, it can be primarily purified to be in relatively high purity by loading the culture supernatant to the cation exchange resin column. The isoelectric point (pI) is the pH at which a protein molecule has zero net charge meaning the electrical charge of the electrical double layer of the protein molecule is zero. When a protein dissociates from its bound complex, the number of cation is equal to that of anion, and thus its net charge becomes zero. The antibody to be purified in the present invention may include, but is not limited to, those having an isoelectric point of preferably 7 to 11, and more preferably 8 to 10. In addition, the antibody of the present invention may include, but is not limited to, preferably all of the antibodies with therapeutic potential which are commonly used in the art, more preferably, a HER-2 (Human Epidermal Growth Factor Receptor 2)-targeting antibody, namely trastuzumab or pertuzumab, and most preferably trastuzumab. Trastuzumab is developed by Genentech (USA) and also called as Herceptin. It is a humanized antibody targeting HER2 and is known as a therapeutic antibody for HER2/neu which is mostly found in breast cancer cells.

As used herein, the term "active antibody" refers to a main constituent included in the population of antibodies that is prepared by the method of the present invention. And it refers to an antibody that does not have a reduced biological activity which may caused by modification such as deamidation or oxidation of some amino acids in the antibody. That is, an active antibody refers to an antibody that is not an acidic or basic antibody isoform. The active antibody is the most important constituent for the quality of the population of antibodies, and has the highest biological activities among other constituents of the antibody.

As used herein, the term "an antibody isoform" refers to an antibody modified by deamidation or oxidation of certain amino acids in active antibodies, and it includes acidic antibody isoform and basic antibody isoform. Examples of the isoforms include an antibody isoform wherein asparagine is deaminated to aspartate or an antibody isoform wherein methionine is oxidized to methionine sulfate. In addition, glutamate at the N-terminal of heavy chain may form a five-membered ring structure and be transformed to pyroglutamate yielding an antibody isoform. If the antibody isoforms are produced in the host cell such as CHO cell line, the antibody products contain a high proportion of isoforms in the cell culture.

Therefore, those antibody isoforms need to be removed through a purification process such as chromatography so that the population of antibodies comprises a desired proportion of active antibodies and antibody isoforms. Likewise, in order to obtain a population of antibodies with high quality from the culture supernatant, the antibody isoforms need to be removed to an acceptable range so the population comprises a desired proportion of active antibodies. In addition, for the purpose of producing antibodies with high purity, the impurities such as host cell protein (HCP), host cell-derived DNA (HCD), and growth factors have to be removed from the population of antibodies. In this regard, the present invention provides a method for preparing the population of antibodies by regulating the amount of antibody isoforms and effectively removing other impurities such as host cell proteins.

In the present invention, the step (a) is for collecting the eluate which is a purified form of the sample that comprises a mixture of antibodies to have the reduced amount of host cell proteins (HCPs) and antibody isoforms thereof. To be more specific, The step (a) is for removing host cell proteins (HCPs) and antibody isoforms from the sample by (i) loading a sample comprising a mixture of antibodies to a pre-equilibrated cation exchange column, (ii) then optionally washing the column with an wash buffer, and (iii) eluting antibodies bound to the column with an elution buffer.

As used herein, the term "a sample comprising a mixture of antibodies" refers to a partially purified culture supernatant or extract of antibody-producing cells which comprise both active antibodies and antibody isoforms. When the antibodies are produced in the host cells, the mixture of active antibodies and antibody isoforms is present in the culture supernatant or cell extract. The "partially purified" means that proteins other than the desired antibodies are remained even after one or repeated fractionation processes such as filtering.

The sample comprising the mixture of the antibodies may be prepared by a method comprising (a) culturing host cells to produce the antibodies, and removing the host cells to prepare a culture supernatant; and (b) adjusting pH of the culture supernatant to the pH lower than the isoelectric point of the target antibody, preferably pH 4 to 6, to form the precipitates and remove them.

If the pH is adjusted before removing the cells in the cell culture, a lower pH promotes cell death, increasing the amount of host cell proteins in the culture. Therefore, pH of the cell culture needs to be modulated after removing the cells in order to reduce the amount of host cell proteins. And the sample prepared by this method can be used for more efficient purification of the antibody population.

The method of removing cells may be the typical method known in the art, and it may be preferably performed by using a filter, and more preferably a depth filter, but is not limited thereto. In an embodiment of the present invention, it was found that when the pH value of the cell supernatant recovered by primary filtration of cells was reduced to 5, and then the cell supernatant was subjected to re-filtration, the content of host cell proteins is remarkably low, compared to the sample for loading of the cation exchange column, which was prepared by filtration after reduction of the pH value of the cell-containing culture broth to 5 (Table 2 and FIG. 1).

Antibodies having a high isoelectric point do not form aggregates in an acidic condition with low pH, whereas host cell proteins (HCP) having a lower isoelectric point than the antibodies have no net charge in an acidic condition with low pH, thereby forming aggregates by van der Waals force and a large amount of precipitates are produced. Therefore, the pH range of the culture supernatant may be set lower than an isoelectric point of the desired antibody but close to an isoelectric point of the host cell proteins, in order to increase the precipitation of the host cell proteins. That is, the pH may be lower than the isoelectric point of the desired antibody by a scale of preferably 1 to 6 and more preferably 2 to 5. Consequently, the pH of the supernatant may be in a range preferably from 3 to 7, more preferably from 4 to 6, and most preferably from 4.5 to 5.5. The precipitates resulted from adjusting the pH of the supernatant may be removed by a filter which is commonly used in the art (e.g., a sterile filter). In one embodiment of the present invention, it was found that when the precipitates are formed by reducing the pH to 5 and are removed from the supernatant, the following purification steps can be performed more efficiently yielding more purified product.

In addition, a condition of the sample may be adjusted to have a conductivity of 5 to 7 mS/cm, before loading the sample, but is not limited thereto.

In the preparation method of the present invention, the step (a) comprises a step of loading the sample prepared by the above method to the pre-equilibrated cation exchange column, optionally washing the column with a wash buffer, and eluting antibodies bound to the column with an elution buffer.

As used herein, the term "cation exchange column" refers to a column packed with a cation exchange resin. In the above step, cation exchange chromatography can be performed to remove antibody isoforms of the active antibody and impurities, preferably host cell proteins (HCP). The cation exchange resin means a synthetic resin that exchanges its own cations with other cations in an aqueous solution. Because antibodies have high isoelectric point, they are positively charged in a buffer solution having a pH value lower than the isoelectric point. Therefore, the cation exchange resin capable of adsorbing the positively charged antibodies is used for improving the quality of the population of antibodies. The cation exchange resin may be chosen from those typically used in the art, but is not limited to, and it could be preferably a column having a functional group of $COO^-$ or $SO_3^-$, and more preferably, carboxymethyl (CM), fractogel, sulfoethyl (SE), sulfopropyl (SP), phosphate (P) or sulfonate (S), and much more preferably, carboxymethyl sepharose (CM sepharose) or fractogel $COO^-$.

The step (a) is characterized in that it can remove both the host cell proteins and antibody isoforms of the active antibody.

In this regard, the host cell proteins may include all different forms of impurities excluding the desired antibodies. Specifically, it may include all of the host cell-derived DNAs, cell growth factors, host cell proteins themselves, and the like. Therefore, if these host cell proteins can be removed effectively, the remaining desired antibodies can be purified much easily yielding antibody product having high purity.

Further to the above step, antibody isoforms need to be removed in order to prepare the population of antibodies with high quality. The antibody isoforms may be an acidic antibody isoform and/or a basic antibody isoform. In general, a variety of antibody isoforms are present in the antibody products expressed in the host cells. When producing biosimilar antibodies, it is important to prepare products with high degree of similarity to the reference drug in terms of product quality. Since antibody isoforms have a different charge than the active antibodies due to the modification of several amino acids, they can be isolated from the desired antibodies based on this charge difference. However, the charge difference is very small since it was caused by only a few amino acids, and thus for purification, a precise condition needs to be set up for purification. For this reason, a cation exchange column is used in the present invention to remove the acidic antibody isoform and/or the basic antibody isoform.

The antibody isoforms refer to antibodies resulting from modification by deamidation or oxidation of few amino acids in the antibody. Since the antibody isoforms have different biological activities, it is important to maintain the amount of antibody isoforms at a constant level for a quality control. In general, the culture supernatant contains a high proportion of acidic and basic antibody isoforms relative to the active antibodies. Thus, the proportion of three different types of the antibodies should be adjusted by reducing the amounts of antibody isoforms. A preferred proportion of the active antibodies in the population of antibodies is 65% or more, while a preferred proportion of the basic antibody isoform is 20% or less. In step (a), the proportions of the active antibody, acidic antibody isoform, and basic antibody isoform are controlled to be preferably in a range from 65 to 80%, 15 to 30%, and 5 to 20%, respectively.

In the above step (a), the washing process may preferably comprise the following steps: the first washing step that allows adsorption of remaining antibodies to the column; the second washing step for the secondary equilibration of the column; the third washing step that removes acidic antibody isoforms; and the fourth washing step that allows re-adsorption of acidic antibody isoforms that were not removed during the third washing step. The pH and composition of buffer solution for the above washing steps 1 to 4 can be adjusted depending on the type of antibody isoforms to be removed or the type of column used in the purification process.

In order to remove the acidic antibody isoforms from the sample comprising a mixture of antibodies, a carboxymethyl sepharose (CM sepharose) may be used preferably. In a preferred embodiment of the present invention, the antibody purification was performed by using CM sepharose having a $COO^-$ group. The results demonstrated that there was no difference between using CM sepharose and Protein A in terms of product yield and purity. And the use of CM sepharose allowed production of antibodies having higher product yield and purity than the use of SP (Table 4).

Figure 4:
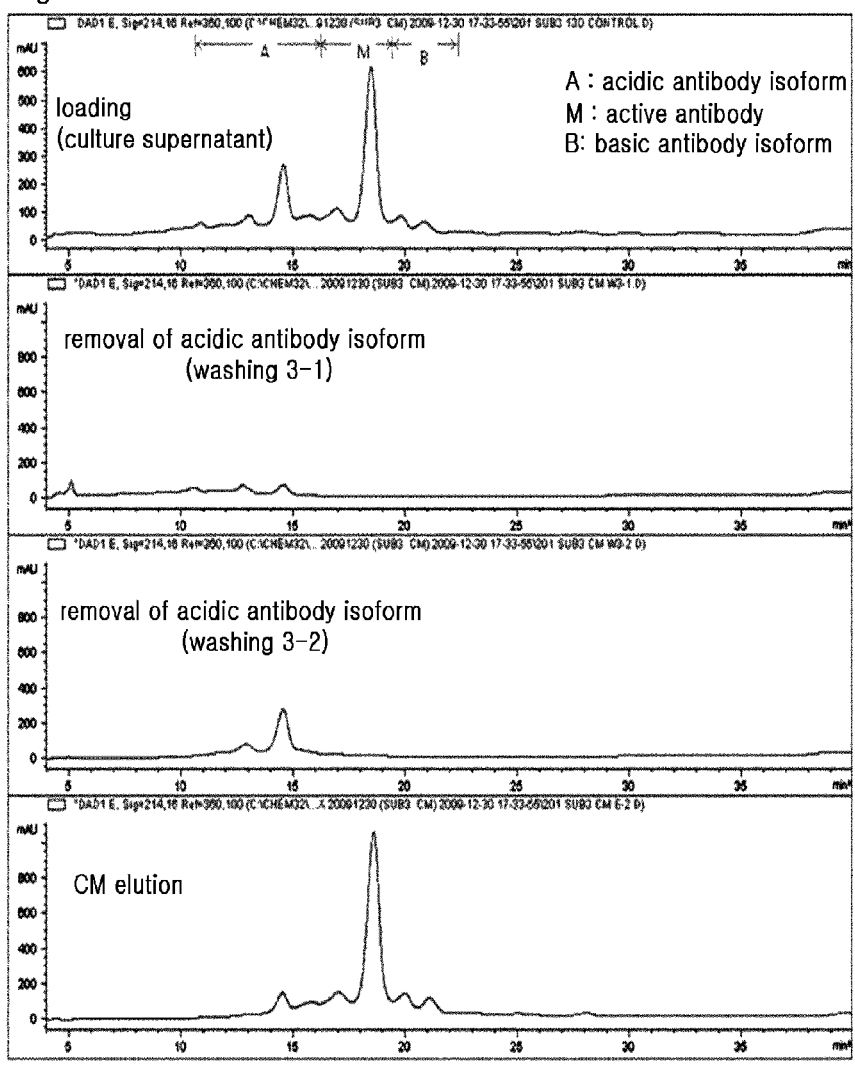
FIG. 4 shows a graph of CEX HPLC, in which purification was performed using the CM column.

The preparation method that uses carboxymethyl sepharose may preferably comprise (i) loading the sample to the carboxymethyl sepharose (CM sepharose) column pre-equilibrated with an equilibration buffer comprising 20 to 30 mM sodium acetate (pH 4.5 to 5.5) and 35 to 45 mM sodium chloride (NaCl); (ii) washing the column with a buffer comprising 20 to 30 mM sodium acetate (pH 4.5 to 5.5) and 35 to 45 mM sodium chloride; (iii) washing the column with a buffer comprising 20 to 30 mM Tris-hydrogen chloride (Tris-HCl) (pH 7.0 to 7.5); (iv) washing the column with a buffer comprising 20 to 30 mM Tris-hydrogen chloride (pH 7.0 to 7.5) and 20 to 30 mM sodium chloride; (v) washing the column with a buffer comprising 20 to 30 mM Tris-hydrogen chloride (pH 7.0 to 7.5); and (vi) eluting antibodies from the column with an elution buffer comprising 20 to 30 mM Tris-hydrogen chloride (pH 7.0 to 7.5) and 80 to 100 mM sodium chloride. In an embodiment of the present invention, it was found that the antibody was purified via the steps of equilibration-loading-washing 1-washing 2-washing 3-washing 4-detachment-stripping-column regeneration (Table 5), thereby increasing the content of the active antibody to 10% or more (FIG. 4, Table 7).

Furthermore, the removal of both the acidic antibody isoform and the basic antibody isoform may be preferably done by using fractogel $COO^-$.

If a large amount of the basic antibody isoforms are mixed with the acidic antibody isoforms, a cation exchange column that can remove both acidic antibodies and basic antibodies is necessary to prepare the desired population of antibodies. In this case, the acidic antibody isoforms and the basic antibody isoforms can be removed at the same time by using fractogel $COO^-$ composed of a synthetic methacrylate polymer resin as a support, unlike CM that has a $COO^-$ functional group but is composed of a sepharose-based support. In one embodiment of the present invention, when antibody purification was performed using fractogel $COO^-$, the basic antibody isoform as well as the acidic antibody isoform could be effectively removed (Table 7 and FIG. 8).

Figure 6:
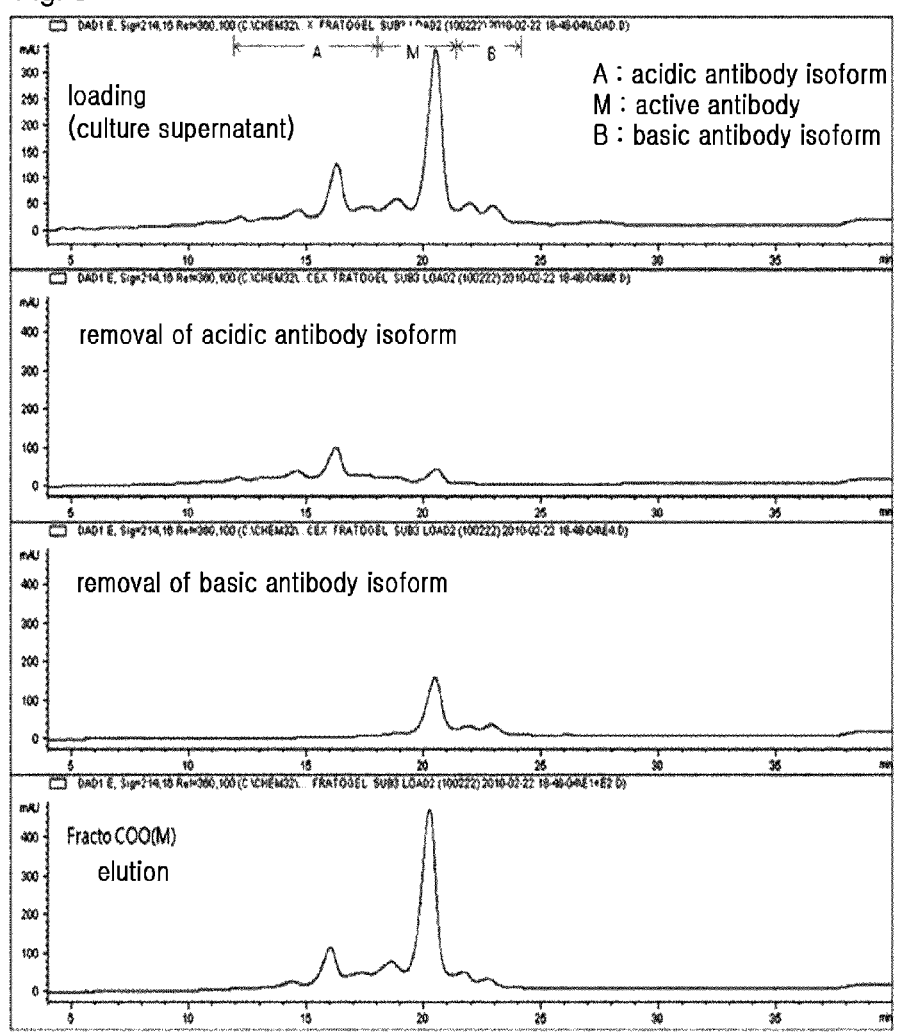
FIG. 6 shows a graph of CEX HPLC, in which purification was performed using the Fractogel COO$^-$ (M) column.

The preparation method using fractogel $COO^-$ may preferably comprise (i) loading the sample to the fractogel $COO^-$ column pre-equilibrated with an equilibration buffer comprising 20 to 30 mM sodium acetate (pH 4.5 to 5.5) and 35 to 45 mM sodium chloride (NaCl); (ii) washing the column with a buffer comprising 20 to 30 mM sodium acetate (pH 4.5 to 5.5) and 35 to 45 mM sodium chloride; (iii) washing the column with a buffer comprising 25 to 35 mM sodium acetate (pH 5.5 to 6.5); (iv) washing the column with a buffer comprising 25 to 35 mM sodium acetate (pH 5.5 to 6.5) and 45 to 55 mM sodium chloride; (v) washing the column with a buffer comprising 25 to 35 mM sodium acetate (pH 5.5 to 6.5); and (vi) eluting antibodies from the column with an elution buffer comprising 25 to 35 mM sodium acetate and 70 to 90 mM sodium chloride. In an embodiment of the present invention, it was found that the antibody was purified via the steps of equilibration-loading-washing 1-washing 2-washing 3-washing 4-detachment-stripping-column regeneration (Table 6), thereby increasing the content of the active antibody to 14% or more and decreasing the content of the basic antibody isoform to approximately 4% or more (FIG. 6 and Table 7).

In the present invention, the step (b) is for collecting an eluate from the hydrophobic interaction column (HIC), which has a reduced amount of HCPs compared to the eluate from step (a). To be more specific, the step (b) comprises (i) loading a sample prepared by mixing the eluate of step (a) with salts, to hydrophobic interaction column (HIC) which is pre-equilibrated with an equilibration buffer, and (ii) eluting the antibodies bound to the column with an elution buffer.

The eluate of antibodies collected from the step (a) may be the initially collected eluate or a diluted form thereof with an additional buffer. The sample for hydrophobic interaction chromatography may be prepared by adding salts to the eluate of step (a). The type of salt added to the sample is not limited, but in one embodiment of the present invention, sodium citrate was added to the eluate of step (a). In addition, a salt concentration of the above sample may be adjusted to be 0.8 to 1.2 times higher than that of the equilibration buffer used in the hydrophobic interaction column in step (b), and more preferably the sample may be prepared by adding salts to the eluate of antibodies from step (a) so it can have the same salt concentration as the equilibration buffer, but is not limited thereto.

In addition, the above step (b) can preferably elute the antibody in a linear-concentration gradient. In an embodiment of the present invention, the concentration-gradient elution is more effective than step-wise elution in terms of yield and elution volume (Example 3).

The above step (b) is to increase the purity of antibody products by removing impurities such as host cell proteins that were not removed during step (a). The step (b) uses hydrophobic interaction column and it can remove host cell proteins based on the difference in hydrophobicity, which has a different separation mechanism from cation exchange column of step (a).

As used herein, the term "hydrophobic interaction column (HIC)" refers to a column packed with hydrophobic interaction resins. In the above step, hydrophobic interaction chromatography is performed to remove impurities, preferably host cell proteins. The tertiary structure of protein is generally hydrophilic, but the protein has a hydrophobic portion as well within its overall structure. And a hydrophobicity of this portion does not arise under the condition where an electrostatic interaction between proteins is strong. But if an ionic strength or permittivity of a solvent is increased making the electrostatic interaction weak, then the hydrophobicity of the protein will become relatively stronger. In this regard, if a hydrophobic ligand (long hydrocarbon chain or aromatic ring) is introduced into a hydrophilic chromatography support (agarose gel piece, organic polymer support, etc.) and equilibrated with salts at a high concentration, a variety of proteins can be adsorbed to these ligands. Subsequently, as the salt concentration is decreased, proteins can be separated easily as they are eluted according to their properties. That is, when a hydrophobic environment is made by adjusting a salt concentration, proteins will have different adsorption strength to a specific column based on their hydrophobicity. Using this principle, the step (b) can be performed to remove HCP using the hydrophobic interaction column.

The hydrophobic interaction resin can be chosen from those commonly used in the art, but is not limited to. Preferably it includes a phenyl column, a butyl column, a phenyl sepharose or fractogel EMA phenyl column, etc., and more preferably phenyl sepharose.

The step (b) using the hydrophobic interaction column may comprise preferably the following steps, (i) loading a sample prepared by adjusting a sodium citrate concentration of the eluate of step (a) to be the same as in an equilibration buffer comprising 25 to 35 mM sodium acetate (pH 5.5 to 6.5) and 0.3 to 1.0 M sodium citrate, to hydrophobic interaction column (HIC) which is pre-equilibrated with the equilibration buffer; and (ii) eluting the antibodies with an elution buffer comprising 25 to 35 mM sodium acetate (pH 5.5 to 6.5) in a linear gradient.

In one embodiment of the present invention, when an sodium acetate buffer of pH 6.0 was used, the product yield was higher, as compared to when Tris-hydrogen chloride was used. Furthermore, the gradient elution showed a high product yield, as compared to a step-wise elution (Table 9). These results demonstrate that the above method involving a gradient elution is an efficient way for preparing a population of antibodies having high purity.

In the present invention, the step (c) is to collect a desired population of antibodies by removing the impurities from the eluate obtained from step (b). Specifically, the above step (c) is for collecting flow-through by loading the eluate of step (b) to anion exchange column. Furthermore, the eluate collected from the above step (b) may be the collected eluate itself or a diluted form with additional buffer solution, but is not limited thereto.

As used herein, the term "anion exchange column" refers to a column packed with anion exchange resins. In the above step, anion exchange chromatography can be performed to remove impurities, preferably host cell proteins. The anion exchange resin refers to a synthetic resin that exchanges its own anions with other anions in a solution. The anion exchange column can adsorb protein that are negatively charged at the pH higher than its isoelectric point. Since the antibodies have a high isoelectric point, when a neutral buffer solution is used, those antibodies will not bind to the resin but instead flow through the column. On the other hand, impurities such as host cell proteins have a low isoelectric point and thus will be adsorbed to the anion exchange resin and removed easily. The step (c) can be carried out based on this principle.

The anion exchange resin can be chosen from those commonly used in the art, but is not limited thereto. Examples of such resin include preferably Q sepharose, quaternary aminoethyl, quaternary amine (Q) or the like, and more preferably Q Fast Flow.

In addition, the above method may use an equilibration buffer having pH lower than the isoelectric point (pI) of the target antibodies, preferably a buffer with pH 7.0 to 8.0 and more preferably a buffer containing tris-hydrogen chloride with pH 7.0 to 8.0. In one example of the present invention, when Q Fast Flow was used as an anion exchange resin and Tris-hydrogen chloride as an equilibration buffer, the purity and product yield of the antibodies was higher than when using MES buffer. Also, a range of pH from 7.0 to 8.0 was found to be the most appropriate for separation of antibodies (Table 11).

As described above, the host cell proteins to be removed may include all impurities excluding the desired antibodies, and also include all of the host cell-derived DNAs, cell growth factors or the like, and the host cell proteins themselves. Therefore, if the host cell proteins are removed first, the desired antibodies can be purified more easily with high quality and purity. In addition, in step (c) the anion exchange column can effectively remove endotoxins as well as host cell proteins, thereby purifying the desired population of antibodies with a high purity.

Figure 12:
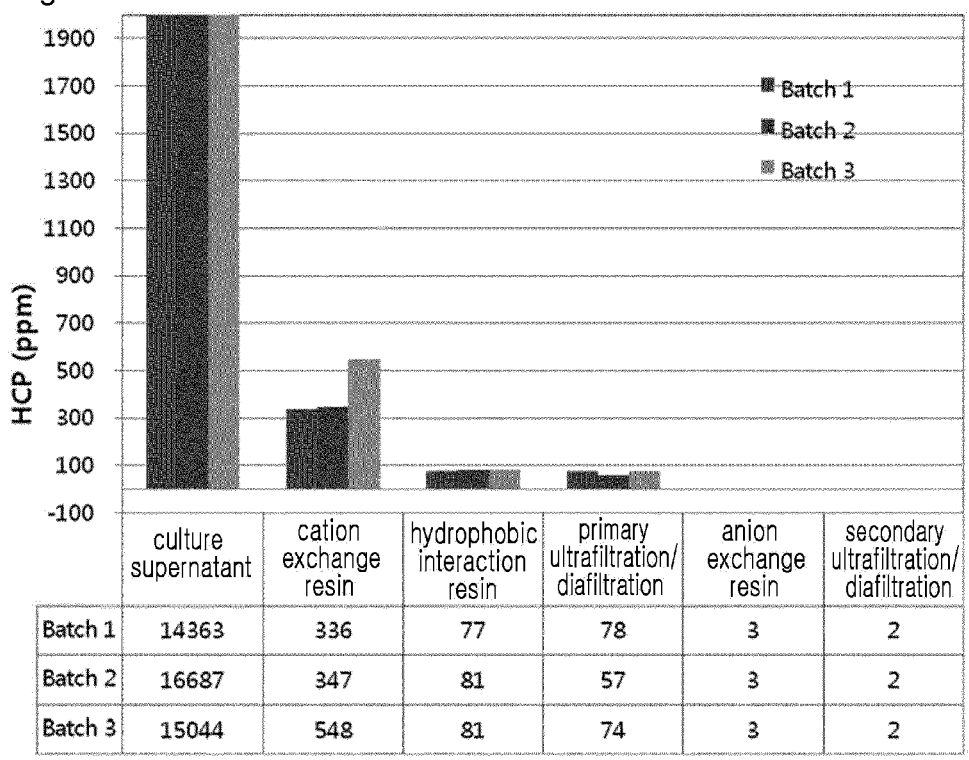
FIG. 12 shows a graph demonstrating the amount of host cell protein (HCP) removed at each step of the antibody purification method of the present invention.

Overall, through the antibody purification method of the present invention comprising the above steps (a) to (c), antibodies can be prepared with high purity and product yield by effectively removing impurities, especially host cell proteins. The concentration of the host cell protein in the final purified sample may be in a range from 0.0001 to 10 ppm preferably, or in a range from 0.001 to 5 ppm more preferably. In one example of the present invention, the concentration of the host cell proteins was reduced to below 550 ppm after the first purification, below 100 ppm after the second purification, and below 5 ppm after the third purification (FIG. 12). Furthermore, in another example of the present invention, it was confirmed that the present antibody purification method can prepare 99.9% pure antibody population (Table 13).

As another aspect, the present invention provides a population of antibodies wherein over 65% of the population are active antibodies prepared by the above method.

The method, the population of antibodies, and the population of antibodies wherein over 65% of the population are active antibodies are the same as described above.

Mode for the Invention

Hereinafter, the present invention will be described in more details referring to each Examples. However, these Examples are for illustrative purposes only, and the invention is not intended to be limited by these Examples.

Example 1. Pre-Treatment of Culture Broth for Antibody Purification

The recombinant trastuzumab antibody-expressing CHO cells (ATCC No. CCL 61) were cultured to express the trastuzumab antibody, and then the pH value was reduced to 6 or lower in order to adsorb the antibody onto the cation exchange column.

In this Example, two methods were performed for comparison. In Method 1, the culture supernatant was recovered by removal of the cells from the culture broth through a primary filtration using a depth filter, and then the pH value of the culture supernatant was reduced to 5, followed by re-filtration of the culture supernatant. In Method 2, the pH value of the cell-containing culture broth was reduced to 5, and then the culture broth was subjected to filtration using the depth filter, so as to prepare a sample for loading of the cation exchange column. The experiment was performed for comparison of the two methods (Table 1).

TABLE 1

Two methods for removing impurities by pH reduction of culture broth

| Procedure | Method 1 | Method 2 |
| --- | --- | --- |
| 1 | Culture broth | Culture broth |
| 2 | Recovery of supernatant by removal of cells using depth filter | pH reduction to 5 by addition of 10% acetic acid to culture both |
| 3 | pH reduction to 5 by addition of 10% acetic acid to supernatant | Low-speed stirring at room temperature (approximately 25° C.) for 1 hour |
| 4 | Low-speed stirring at room temperature (approximately 25° C.) for 1 hour | Recovery of supernatant by removal of cells and precipitates using depth filter |
| 5 | Removal of precipitates by depth and sterile filters, and sterilization | Sterilization by sterile filter and removal of residual precipitates |

For comparison of the two methods, yields and contents of the host cell proteins (HCP) after cation exchange column were compared.

As a result, Method 1 of primarily removing cells showed the yield of 84% and the final content of host cell proteins of 47.3 ppm after cation exchange column. In contrast, Method 2 of directly reducing the pH of culture broth showed the final yield of 82% after pre-treatment and the content of host cell of 110.6 ppm after cation exchange column (Table 2).

TABLE 2

Comparison of yields and HCP contents after cation exchange column in Pre-Treatment Method 1 and Method 2

| Section | Procedure | pH | Viability (%) | Yield (%) | Host cell proteins (HCP, ppm) |
|---|---|---|---|---|---|
| Method 1 | Culture broth | 7.1 | 92.3 | 100 | |
| | Depth filter (removal of cells) | 7.1 | | | |
| | pH Reduction to 5 and 1 hr-low-speed stirring | 5.0 | | 86 | |
| | depth and sterile filters | 5.0 | | 84 | |
| | After cation exchange column | | | | 47.3 |
| Method 2 | Culture broth | 7.1 | 92.3 | 100 | |
| | pH Reduction to 5 and 1 hr-low-speed stirring | 5.0 | 73.9 | | |
| | Depth filter (removal of cells and precipitates) | 5.0 | | 83 | |
| | Sterile filter | 5.0 | | 82 | |
| | After cation exchange column | | | | 110.6 |

The comparison of cell viability showed that cell viability was reduced from 92.3% to 73.9% at 1 hour after pH reduction to 5 in Method 2, and the final content of host cell proteins increased 2 times after cation exchange column.

These results demonstrate that the pre-treatment method of primarily removing cells using a depth filter before processing is suitable for applying for the purification method of the present invention.

In addition, the two methods of removing precipitates by pH reduction to 6 or lower (preferably pH 5) were performed to obtain the supernatant having much higher purity than the initial culture broth (FIG. 1).

Example 2. Cation Exchange Chromatography 2-1. Selection of Cation Exchange Resin As an alternative to the Protein A column, cation exchange column candidates, as shown in Table 3, were selected, and experiments were performed to select a column having a favorable functional group in terms of purity and yield from the cation exchange columns.

Two columns, SP (sulfuric prophyl, strong, GE) having a functional group of $SO_3$ and CM (carboxyl methyl, weekly, GE) having a functional group of $COO^-$, which are the cation exchange resins commonly used in production process, and Protein A FF (GE) as a control group were used to compare their yields and purities for selection of cation exchange resin.

The supernatant was prepared by pre-treatment of the culture broth (Titer: 0.5 mg/mL) according to Method 1 of Example 1, and distilled water was added thereto to reduce the conductivity to 6.4 mS/cm, thereby preparing a sample to be loaded onto the cation exchange resin column.

TABLE 3

Experimental groups for selection of primary column

| Process | Control group rPA FF(Protein A, GE) | Experimental group 1 SP FF(Strong Cation, GE) | Experimental group 2 CM FF(Weekly Cation, GE) |
|---|---|---|---|
| Column | rProtein A FF 20 mL | SP FF 20 mL | CM FF 20 mL |
| Equilibration buffer | 20 mM Tris-HCl pH 7.5 | 20 mM Na-phosphate pH 6.0 | 20 mM Na-phosphatepH 6.0 |
| Loading | 100 mL (0.5 mg/mL)25 mg/mL resin | Con 7 mS/cm or less, (6.4 mS/cm), pH 6.025 mg/mL resin | Con 7 mS/cm or less(6.4 mS/cm), pH 6.025 mg/mL resin |
| Washing 1 buffer | 20 mM Tris-HCl pH 7.5 + 150 mM NaCl | 20 mM Na-phosphatepH 6.0 | 20 mM Na-phosphatepH 6.0 |
| Washing 2 buffer | 20 mM Tris-HCl pH 7.5 | 20 mM Na-phosphate pH 6.0 + 40 mM NaCl | 20 mM Na-phosphate pH 6.0 + 40 mM NaCl |
| Elution buffer | 100 mM glycine HCl pH 3.0 | 20 mM Na-phosphate pH 6.0 + 200 mM NaCl | 20 mM Na-phosphate pH 6.0 + 200 mM NaCl |
| Analysis | Yield (quantification by UV absorbance measurement)Purity (SEC HPLC, TSK3000) | | |

Figure 2:
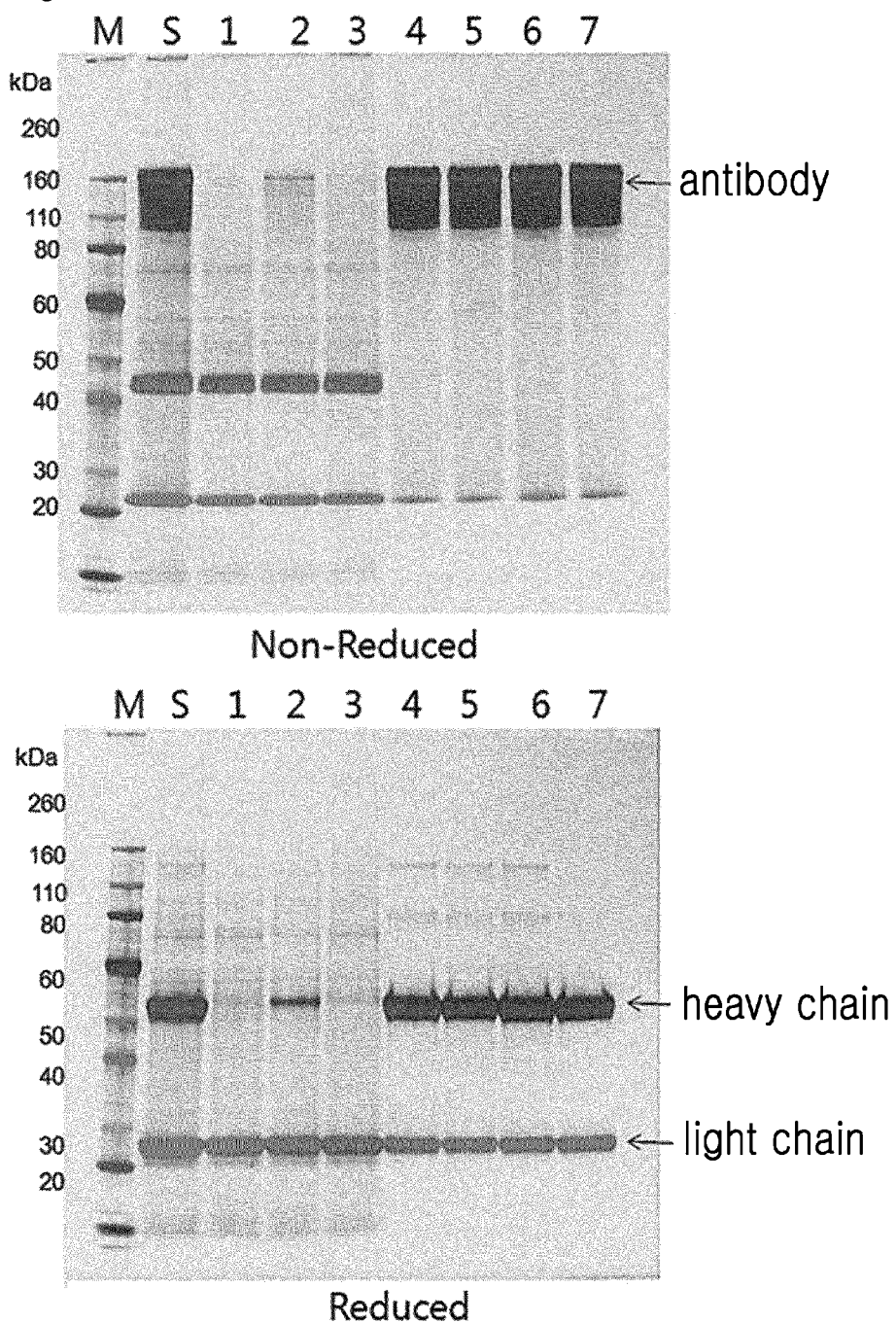
FIG. 2 shows the result of SDS-PAGE comparing the flow-through and eluate collected from a supernatant of cell culture, Protein A column, SP column, or CarboxyMethyl (CM) column, in which M: Protein size Marker, S: supernatant of cell culture, 1: Protein A column flow-through, 2: SP column flow-through, 3: CM column flow-through, 4: Protein A column eluate, 5: SP column eluate, 6: CM column eluate, 7: A reference drug, Herceptin®.

The results of SDS-PAGE under the three conditions showed that, as shown in FIG. 2, antibodies were not detected in the flow-through from the columns of Protein A and CM, whereas antibodies were detected in the flow-through from SP, indicating loss of antibody. When the yields were analyzed by quantifying the concentrations, SP showed a low yield of 2.5% (Table 4). In addition, SP showed the lowest purity of 96.4%, and rPA and CM showed purity of 99.2% and 97.5%, respectively (Table 4).

TABLE 4

Comparison of yield and purity between cation exchange columns SP and CM, and protein A column

| Process | Volume (mL) | Conc. (mg/mL) | Amount (mg) | Step Yield (%) | Purity (%) |
|---------|-------------|---------------|-------------|----------------|------------|
| Culture supernatant | 100 | 0.53 | 53 | | |
| rPA | 16.4 | 3.24 | 53.1 | 100 | 99.2 |
| SP | 53.9 | 0.96 | 51.7 | 97.5 | 96.4 |
| CM | 53.5 | 1.04 | 55.6 | 105 | 97.5 |

These results demonstrate that as the cation exchange resin alternative to the Protein A column for the purification of trastuzumab antibody, CM sepharose having the functional group of $COO^-$ is advantageous over SP in terms of yield and purity.

2-2. Control of Antibody Isoforms Using Cation Exchange Resin CM

Based on the results of Example 2-1, experiments for the control of antibody isoforms using the cation exchange resin CM were performed. The procedure for controlling antibody isoforms using the cation exchange resin CM is as follows.

For equilibration, 6-column volumes of a buffer solution comprising 20 mM sodium acetate (pH 5.0) and 40 mM sodium chloride were applied to the column. The pre-treated supernatant was loaded at a volume lower than the adsorption volume of CM (25 mg/mL column). After loading, Washing 1 was performed to adsorb the unbound antibodies and wash the residual supernatant. Washing 2 was performed for secondary equilibration by applying 10-column volumes of 25 mM Tris HCl (pH 7.2). Washing 3 was performed to remove a part of acidic antibody isoforms by using 25 mM Tris HCl (pH 7.2) and 25 mM sodium chloride. Washing 4 was performed to re-adsorb the acidic antibody isoforms that were remained after removal onto the column, using 25 mM Tris HCl (pH 7.2).

Elution was performed using 25 mM Tris HCl (pH 7.2) and 90 mM sodium chloride to recover the desired population of antibodies. The detailed procedures are shown in the following Table 5.

TABLE 5

Purification procedure for antibody isoforms using cation exchange resin CM

| Procedure | Buffer | Volume |
|-----------|--------|--------|
| Equilibration | 20 mM Sodium Acetate pH 5.0, 40 mM NaCl (6CV) | 6-column volumes |
| Loading | Conductivity Con 6.4 mS/cm or less, adsorption volume: 25 mg/Column mL or less | |
| Washing 1 | 20 mM Sodium Acetate pH 5.0, 40 mM NaCl (5CV) | 5-column volumes |
| Washing 2 | 25 mM Tris HCl pH 7.2 (10CV) | 10-column volumes |
| Washing 3 | 25 mM Tris HCl pH 7.2 + 25 mM NaCl (conductivity 4.86 mS/cm) | 10-column volumes or more |
| Washing 4 | 25 mM Tris HCl pH 7.2 (3CV) | 3-column volumes |
| Detachment | 25 mM Tris HCl pH 7.2 + 90 mM NaCl (3CV) (conductivity 11 mS/cm) | 3-column volumes |
| Stripping | 2M NaCl | 2-column volumes |
| Column regeneration | 1M NaOH | 3-column volumes |

Figure 3:
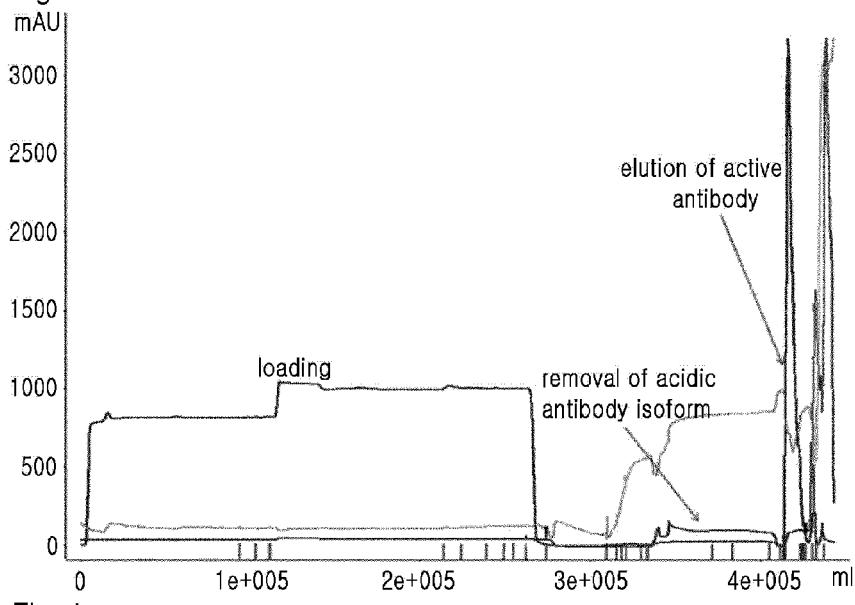
FIG. 3 shows a graph of AKTA process, in which purification was performed using the CM column.

FIG. 3 is a graph showing AKTA Process for the examination of the above procedures. FIG. 4 is a CEX HPLC graph for the analysis of antibody isoform content, in which the peak of acidic antibody isoform was reduced when the active antibody was eluted after removing a part of the acidic antibody isoform in Washing 3.

Therefore, the content of the active antibody was increased to 10% or more by removing the acidic antibody isoform through the above washing procedure.

These results demonstrate that CM column used in the purification method using the cation exchange column effectively removes the portion of acidic antibodies in the population.

2-3. Control of Antibody Isoforms Using Cation Exchange Resin Fractogel COO— (M)

When the antibodies such as Trastuzumab are expressed in animal cells (e.g., CHO cell), the cell supernatant comprises both acidic antibody isoforms and basic antibody isoforms. Therefore, there is a need to identify a cation exchange column suitable for removing both acidic antibody isoforms and basic antibody isoforms from the supernatant.

In detail, the effects of removing the acidic antibody isoform and the basic antibody isoform were examined by using fractogel $COO^-$ (M) composed of a synthetic methacrylate polymer resin as a support, unlike CM that has a $COO^-$ functional group but is composed of a sepharose-based support.

The loading sample was prepared by pre-treatment of the culture supernatant according to Method 1 of Example 1, and loaded at an adsorption volume of 25 mg or less per 1 mL of the Fractogel $COO^-$ (M) resin. The experiment was performed at a linear velocity of 150 cm/hr using the column having a height of 15 cm. The procedure for controlling antibody isoforms using the cation exchange resin Fractogel $COO^-$ (M) is as follows.

Acetate (sodium acetate) was used as a buffer of Fractogel $COO^-$ (M). Washing 1 after loading is a step of attaching the antibody and removing the supernatant from the culture supernatant. Washing 2 is a re-equilibration step of increasing the pH value from 5 to 6 in order to improve separation of the antibody isoforms. Washing 3 is a step of removing the acidic antibody isoform. Washing 4 is a step of re-adsorbing the acidic antibody isoform after removing a part thereof, and Detachment is a step of recovering the desired antibody.

Stripping is a step of removing impurities that were strongly bound to the column. Thereafter, the column was regenerated using 1 M NaOH. The detailed procedures are shown in the following Table 6.

TABLE 6

Purification procedure for antibody isoforms using Fractogel COO⁻

| Procedure | Buffer | Volume |
|---|---|---|
| Equilibration | 20 mM Sodium Acetate pH 5.0, 40 mM NaCl (10 CV) | 10-column volumes |
| Loading | Conductivity Con 6.0 mS/cm or less, adsorption volume: 25 mg/column mL or less | |
| Washing 1 | 20 mM Sodium Acetate pH 5.0, 40 mM NaCl (5 CV) | 5-column volumes |
| Washing 2 | 30 mM Sodium Acetate pH 6.0 (10 CV) | 10-column volumes |
| Washing 3 | 30 mM Sodium Acetate pH 6.0, 50 mM NaCl (10 CV) | To peak |
| Washing 4 | 30 mM Sodium Acetate pH 6.0 | 2-column volumes |
| Detachment | 30 mM Sodium Acetate pH 6.0, 80 mM NaCl | Until reascension |
| Stripping | 2M NaCl | 2-column volumes |
| Column regeneration | 1M NaOH | 3-column volumes |

Figure 5:
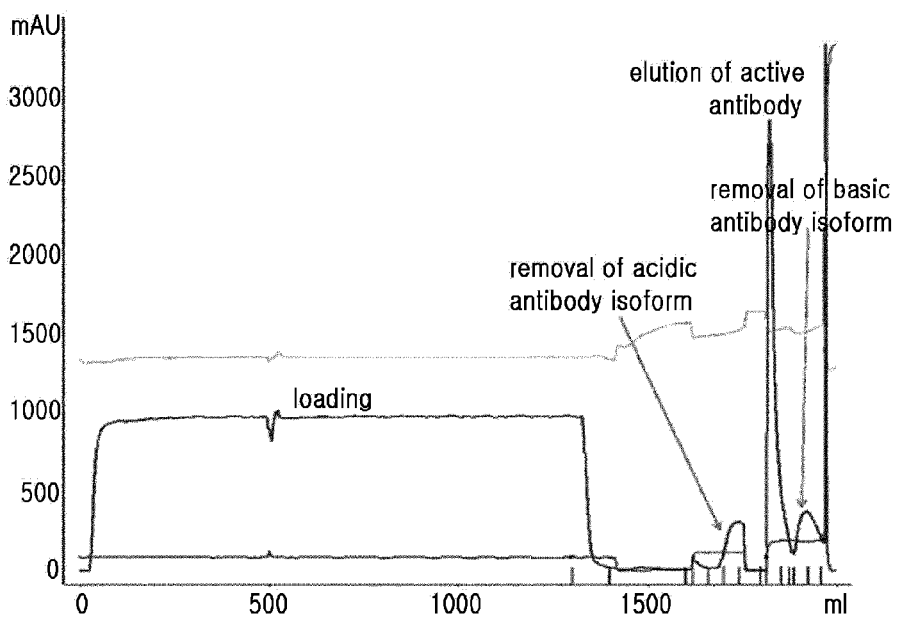
FIG. 5 shows a graph of AKTA process, in which purification was performed using the Fractogel COO$^-$ (M) column.

FIG. 5 is a graph showing AKTA Process of performing purification using Fractogel COO⁻ (M). As shown in the UV peak of the graph, a peak of a large amount of acidic antibody isoforms was observed at the step of Washing 3 after loading, and a peak of the desired antibody eluted was observed at the detachment step, followed by a peak of a large amount of basic antibody isoforms. As shown in the CEX-HPLC graph of FIG. 6, when the desired antibodies were eluted after removing a part of the acidic antibody isoforms and the basic antibody isoforms, the content of active antibody was 14% higher than that of the initial loading sample.

Figure 7:
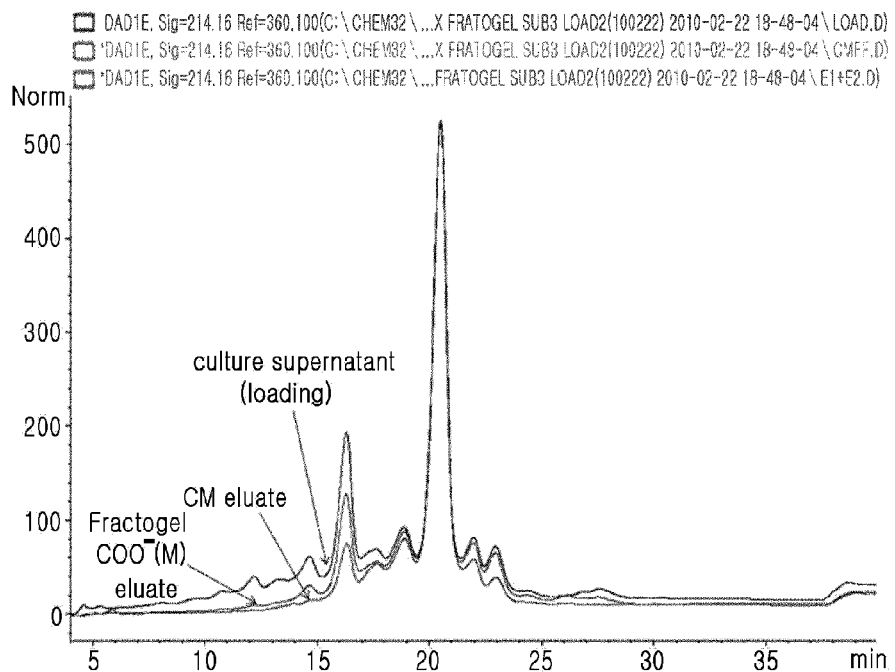
FIG. 7 shows a graph of CEX HPLC of the culture supernatant, the eluate of the CM column, and the eluate of the Fractogel COO$^-$ (M) column.
Figure 8:
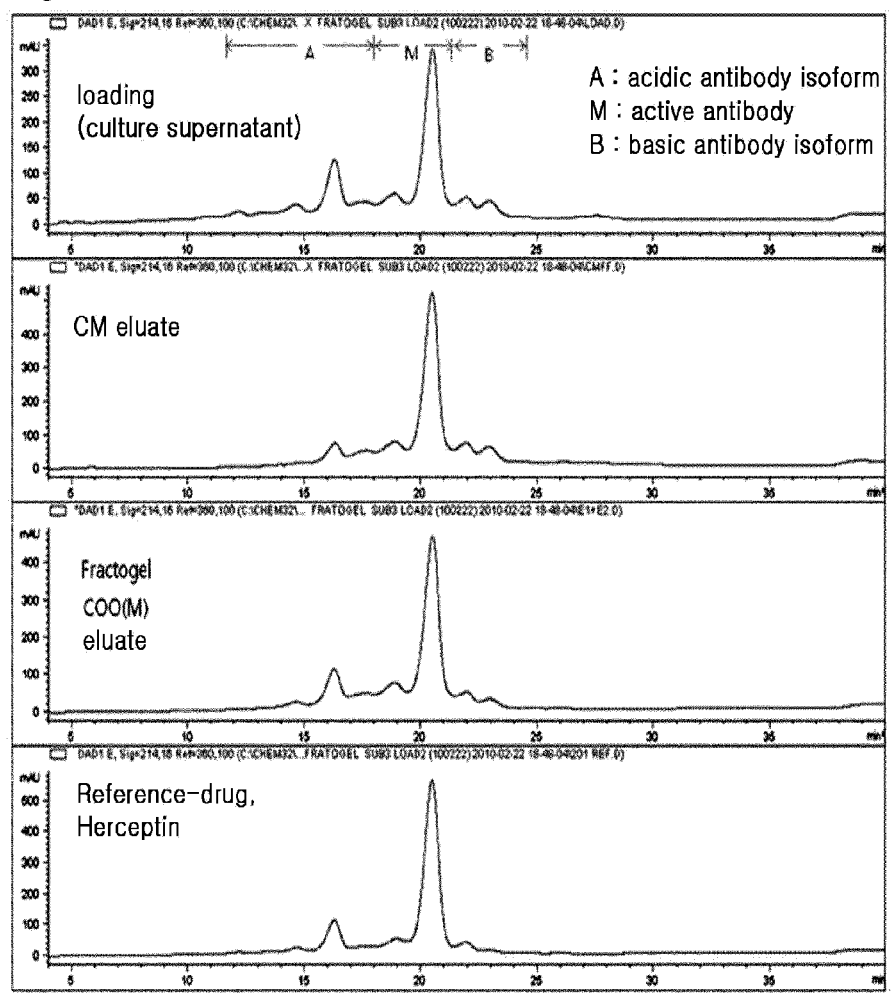
FIG. 8 shows a graph of CEX HPLC of the supernatant of cell culture, the eluate of the CM column, the eluate of the Fractogel COO$^-$ (M) column, and the reference drug, Herceptin®.

As shown in FIGS. 7 and 8; and Table. 7, the removal efficiency of the basic antibody isoform was approximately 8% higher than that of the CM column. The content of basic antibody isoform in the reference drug, Herceptin® was less than 10%. When the culture broth containing a large amount of basic antibody isoforms was purified using the Fractogel COO⁻ (M) column, the basic antibody isoforms as well as the acidic antibody isoforms were efficiently removed (Table 7; and FIGS. 7 and 8).

TABLE 7

Quality comparison by CEX-HPLC analysis

| Section | Content of acidic antibody isoform (%) | Content of active antibody (%) | Content of basic antibody isoform (%) |
|---|---|---|---|
| Quality of Loading (culture supernatant) | 34.0 | 54.7 | 11.3 |
| Quality of active antibody eluted by Fractogel COO⁻(M) | 23.8 | 68.7 | 7.5 |
| Quality of active antibody eluted by CM | 18.4 | 66.3 | 15.3 |
| Quality of Herceptin, reference drug | 22.3 | 71.1 | 6.6 |

2-4. Control Condition of Basic Antibody Isoforms Using Cation Exchange Resin Fractogel COO— (M)

In this Example, a method for adjusting the separation content of basic antibody isoforms by controlling the washing volume in the purification procedures was developed.

In order to adjust the separation content of the basic antibody isoforms, the washing volume was controlled in the step of Washing 4 just before elution of the active antibody. The content of basic antibody isoforms was found to be adjusted. Washing 4 is a step of re-adsorbing the acidic antibody isoforms after removing them. The experiment was performed under the assumption that different elution peaks appear depending on re-adsorption degree.

Figure 9:
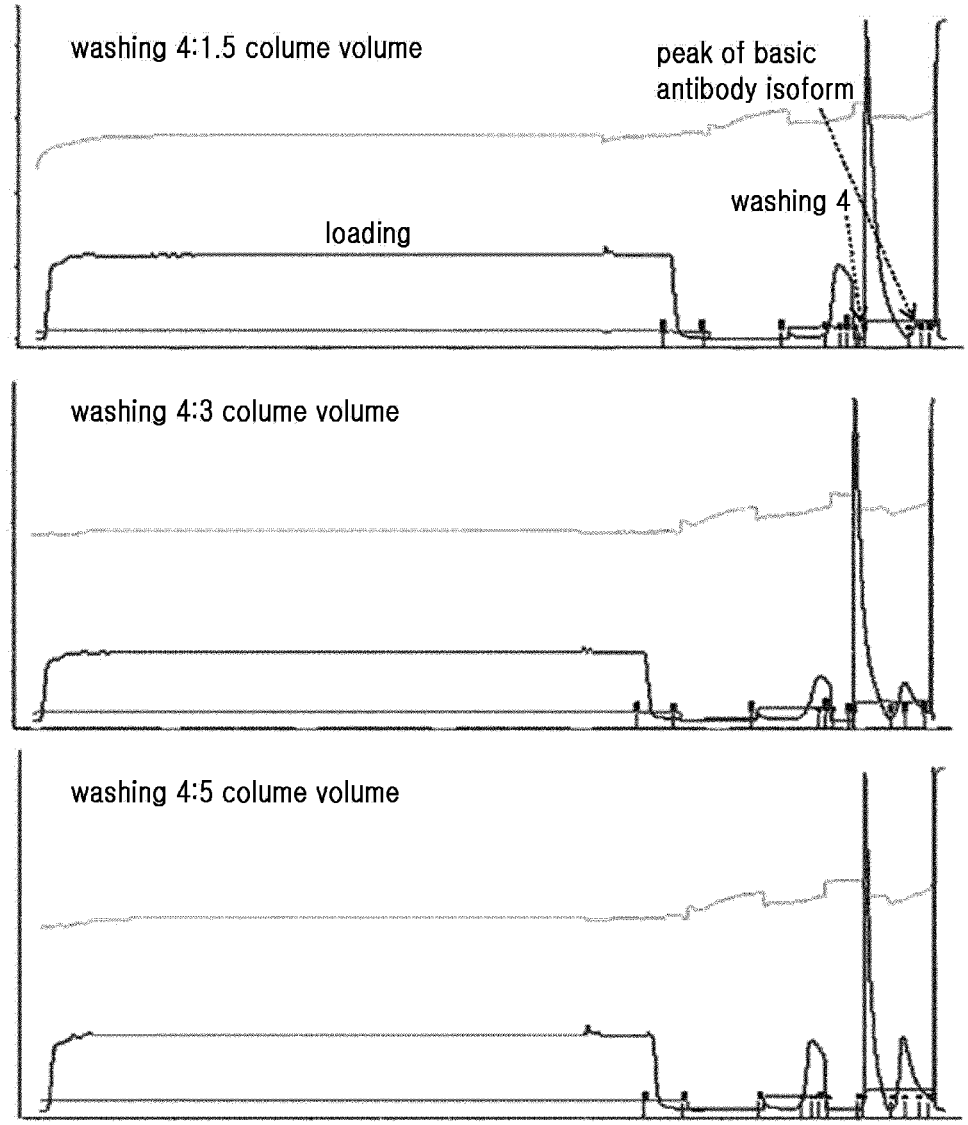
FIG. 9 shows a graph of AKTA process showing changes in the peaks for basic antibody isoforms depending on the volume of a column during 4 steps of washing process in purification method that uses Fractogel COO$^-$ (M) column.

In the step of Washing 4, elution was performed using 1.5-, 3-, and 5-column volumes. As a result, as the column volume increased, the elution peak of the basic antibody isoforms increased (FIG. 9). The major elution samples were analyzed using CEX-HPLC. As a result, when the column volumes were increased in the step of Washing 4, the contents of basic antibody isoforms were reduced in the major elution samples (Table 8). If the contents of the acidic and basic antibody isoforms in the culture broth are higher than those in the reference drug, the method of the present invention can be used to produce the acidic antibody isoform, the active antibody, and the basic antibody isoform in the contents similar to those in the reference drug (Table 8).

TABLE 8

Content changes in CEX HPLC by variation of washing volume in Washing 4 step of Fractogel COO⁻

| Section | Washing 4 volume (column volume) | Content of acidic antibody isoform (%) | Content of active antibody (%) | Content of basic antibody isoform (%) | Yield (%) |
|---|---|---|---|---|---|
| Loading (culture supernatant) | — | 40.0 | 52.5 | 7.5 | |
| Fracto washing 4 (1.5CV) | 1.5 | 26.0 | 65.2 | 7.2 | 71 |
| Fracto washing 4 (3CV) | 3 | 33.6 | 61.3 | 5.1 | 62 |
| Fracto washing 4 (5CV) | 5 | 22.3 | 71.1 | 3.2 | 52 |
| Herceptin ®, the reference drug | — | 19.3 | 74.9 | 5.8 | |

Example 3. Column Conditions for Hydrophobic Interaction Chromatography

The experiment for the purification of high-purity antibody was performed by a hydrophobic interaction chromatography (HIC), phenyl sepharose fast flow.

For the HIC column, the cation exchange resin Fractogel COO⁻ (M) was performed in the same manner as in Example 2-4, and the eluate was used to perform the experiment under the three conditions as in Table 9.

First, in Experimental group (A), adsorption was performed using Tris HCl (pH 7.2) as a basic buffer and 0.6 M sodium citrate, and elution was performed using 100% elution buffer (salt-free buffer) by stepwise elution. In Experimental group (B), adsorption was performed using sodium acetate (pH 6.0) as a basic buffer and 0.6 M sodium citrate, and elution was performed by stepwise elution as in Experimental group (A). In Experimental group (C), adsorption was performed using sodium acetate (pH 6.0) as a basic buffer and 0.6 M sodium citrate, and elution was performed by gradient elution with 5-column volumes of the elution buffer.

The buffer and pH, and the elution method were selected by comparing the three methods.

Two types of buffers, Tris HCl (pH 7.2) and sodium acetate (pH 6.0) were used for comparison, because sodium acetate (pH 6.0) is used as a basic buffer in the cation exchange resin, and Tris HCl is used as a basic buffer in the third column QFF so as to simplify the production process in terms of buffer preparation.

As shown in the graph of AKTA process of FIG. 10, the major elution peaks were split under the conditions of (A) and (B), and the elution volumes were also 2 times higher than that under the condition of (C). However, the elution peak was stable without splitting under the condition of (C), and the elution volume was also the lowest among the three conditions. The lower elution volume is advantageous in that the working time of the next step can be reduced. The results of comparing the three conditions showed that the gradient elution with 5-column volumes of the elution buffer was the most excellent than the stepwise elution in terms of yield, and the sodium acetate buffer (pH 6.0) showed 5% higher yield than the Tris HCl buffer (pH 7.2), and thus the sodium acetate buffer (pH 6.0) was the most suitable HIC buffer because low pH condition is stable in terms of antibody stability against pH (Table 9).

TABLE 9

Conditions for hydrophobic interaction chromatography (HIC) column

| Experimental group | Conditions | HIC elution volume (column volume) | Purity (%) | Yield (%) |
|---|---|---|---|---|
| Loading | Fractogel COO⁻(M) eluate | | 99.4 | — |
| (A) | HIC loading solution: Fractogel COO⁻(M) eluate + equal volume of a buffer comprising 50 mM Tris HCl pH 7.2 and 1.2M sodium citrate/Equilibration buffer: 25 mM Tris HCl pH 7.2 + 0.6M sodium citrate/Elution conditions: 25 mM Tris HCl pH 7.2 (stepwise elution) | 10 | 99.4 | 70 |
| (B) | HIC loading solution: Fractogel COO⁻ (M) eluate + equal volume of a buffer comprising 60 mM sodium acetate pH 6.0 and 1.2M sodium citrate/Equilibration buffer: 30 mM sodium acetate pH 6.0 + 0.6M sodium citrate/Elution buffer: 30 mM sodium acetate (stepwise elution) | 13 | 99.6 | 75 |
| (C) | HIC loading solution: Fractogel COO⁻(M) eluate + equal volume of a buffer comprising 60 mM sodium acetate pH 6.0 and 1.2M sodium citrate/Equilibration buffer: 30 mM sodium acetate pH 6.0 + 0.6M sodium citrate/Elution conditions: 30 mM sodium acetate(gradient elution with 5-column volumes) | 6 | 99.6 | 90 |

Example 4. Conditions for Anion Exchange Chromatography

The present invention developed a purification method for preparing a population of high purity antibodies by using cation exchange resin and hydrophobic interaction resin successively, and then using anion exchange resin chromatography.

Specifically, anionic proteins at the pH above isoelectric point can adsorb to the anion exchange column. Thus antibodies with an isoelectric point higher than 7 (for example, Trastuzumab with an isoelectric point of 8.4), these antibodies cannot adsorb to the anion exchange resin and will elute as a flow-through if a buffer solution with pH of 7 is used. In this regard, the inventors have performed the following experiments to specify the conditions of anion exchange resin and buffer solution suitable for the purification process of the present invention.

In this Example, quaternary amine-based Q Fast flow (GE) frequently used as the anion exchange resin in production scale was used to perform purification. For the preparation of a sample to be loaded onto the anion exchange resin, the culture supernatant was subjected to cation exchange column, hydrophobic interaction column (HIC) and primary ultrafiltration/diafiltration to have a proper conductivity and pH. The purity, HCP content and yield were compared under the three buffer conditions of 25 mm MES (pH 6.0), 25 mM Tris HCl (pH 7.0), and 25 mM Tris HCl (pH 8.0) (Table 10).

TABLE 10

Conditions for anion exchange column

| | Experimental group A | Experimental group B | Experimental group C |
|---|---|---|---|
| Buffer | 25 mM Tris | 25 mM Tris | 25 mM MES |
| pH | 8 | 7 | 6 |
| ConductivitymS/cm | 4 or less | 4 or less | 4 or less |
| column | QFF | QFF | QFF |
| Adsorption volume mg/mL resin | 150 | 150 | 150 |
| Concentration of loading solution (mg/mL) | 10 or less | 10 or less | 10 or less |
| Linear velocity (cm/hr) | 150 | 120 | 120 |

The experimental results of the three conditions are shown in Table 11. When the purity or yield, and the HCP content were compared, the buffer of pH 7 or higher was found to be more excellent than the buffer of pH 6. Therefore, the use of Tris HCl buffer of pH 7 to 8 was found to be preferred (Table 11).

TABLE 11

Comparison of purity, HCP content, and yield under three conditions

| Experimental group | Conditions | Column | Purity (%) | HCP (ppm) | Yield (%) |
|---|---|---|---|---|---|
| (A) | Equilibration buffer: 25 mM Tris HCl pH 8.0 | QFF | 99.6 | 1.52 | 98.1 |
| (B) | Equilibration buffer: 25 mM Tris HCl pH 7.0 | QFF | 99.7 | 1.61 | 98.5 |
| (C) | Equilibration buffer: 25 mM MES pH 6.0 | QFF | 99.8 | 2.53 | 97.3 |

Figure 11:
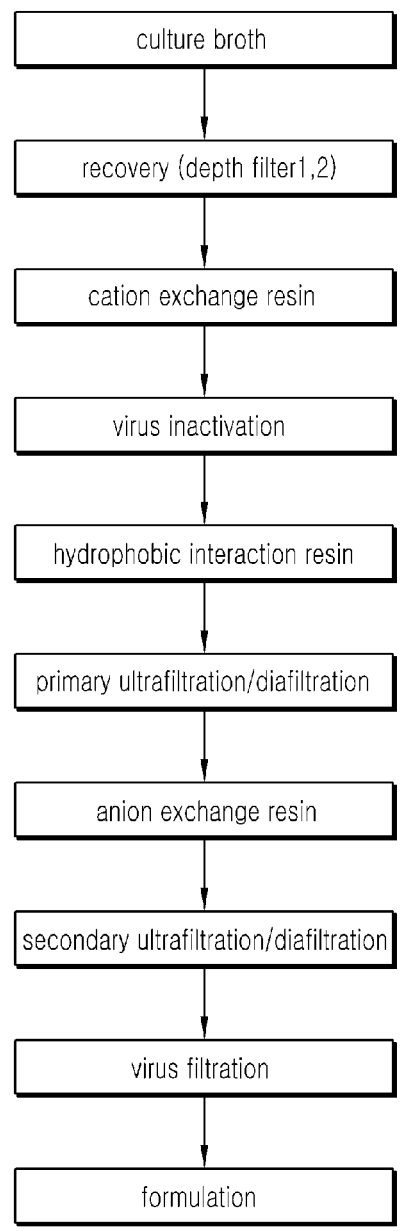
FIG. 11 is a flow chart showing all steps in the antibody purification method of the present invention.

Example 5. Examination of HCP Removal, Purification Yield, and Purity at Each Step of Trastuzumab Process The purification steps of the antibody purification process developed in the present invention, preferably, a purification process of trastuzumab are shown in FIG. 11.

To analyze the HCP content during the process, an ELISA quantification method was performed. HCP quantification of the samples during the purification process of trastuzumab was performed using a CHO host cell protein ELISA kit (Pangen, Cat. PKD1001, Lot. 17011002) coated with anti-CHO HCP antibody against CHO cell proteins. HCP removal at each step of the process was analyzed for 3 batches, which is shown in FIG. 12.

The initial content of HCP was 14000 ppm or more after the recovery process of the culture broth, and the content of HCP was reduced to less than 550 after the cation exchange column, and reduced to less than 100 ppm after HIC process. In addition, it was reduced to less than 5 ppm after the anion exchange resin, thereby producing the host cell protein-removed trastuzumab (FIG. 12).

Next, the purification yields of the 3 batches were calculated. For the yield analysis, the content in the culture broth was analyzed using the protein A column, and then analyzed by UV absorbance measurement after cation exchange resin. As shown in the following Table 12, the step yield was approximately 77 to 79% by the yield loss due to removal of parts of the acidic and basic antibody isoforms for the quality control in the cation exchange resin process after recovery, and a very low yield loss was observed until the purification termination after the cation exchange resin (Table 12).

TABLE 12

Comparison of purification yields between 3 batches

| | Total yield (%) | | |
|---|---|---|---|
| Process | Batch 1 | Batch 2 | Batch 3 |
| Culture broth | 100 | 100 | 100 |
| Recovery | 96.9 | 95.8 | 97.2 |
| Cation exchange resin | 78.6 | 77.0 | 77.8 |
| Virus inactivation | 77.7 | 75.0 | 76.5 |
| Hydrophobic interaction resin | 77.4 | 74.8 | 71.7 |
| Primary ultra-filtration/ diafiltration | 76.5 | 70.7 | 71.7 |
| Anion exchange resin | 73.8 | 69.3 | 70.1 |
| Secondary ultra-filtration/ diafiltration | 76 | 71.6 | 68.1 |
| Virus filtration | 71.5 | 70.3 | 68.7 |
| Formulation | 72.3 | 71.3 | 71.3 |

Next, the purities of the 3 batches were analyzed. For the purity analysis, SE-HPLC (Size Exclusion-High Performance Liquid Chromatography) was used to perform the analysis. TSK-Gel 3000SW$_{xL}$ (Tosoh Bioscience) was used as a column, and each sample was diluted using PBS (Phosphate buffer saline, pH 7.4) to 10 mg/mL, 20 μl thereof was injected for analysis. The analysis was performed at 280 nm using PBS as the mobile phase with a flow rate of 0.5 mL/min for 30 minutes.

As a result, the final purities of the three batches were 99.9%, which was 0.3% higher than the purity of the control drug of 99.6% (Table 13). These results demonstrate that the method of the present invention, which comprises the steps of using cation exchange column, HIC and anion exchange column, may be a effectively used for production of a desired population of antibodies with high purity and high quality.

TABLE 13

Comparison of purities between 3 batches

| | Purity (%) SEC HPLC | | |
|---|---|---|---|
| Process | Batch 1 | Batch 2 | Batch 3 |
| Culture broth recovery | | | |
| Cation exchange resin | 99.7 | 99.1 | 99.7 |
| Virus Inactivation | 99.8 | 98.8 | 99.7 |
| Hydrophobic interaction resin | 99.9 | 99.9 | 99.6 |
| Primary ultra-filtration/ diafiltration | 99.7 | 99.5 | 99.8 |
| Anion exchange resin | 99.8 | 99.6 | 99.6 |
| Secondary ultra-filtration/ diafiltration | 99.8 | 99.9 | 99.9 |
| Virus filtration | 99.9 | 99.9 | 99.9 |
| Formulation | 99.9 | 99.9 | 99.9 |
| Reference drug | | 99.6 | |

While the present invention has been particularly shown and described with reference to the foregoing preferred and alternative embodiments, it should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non obvious combinations of elements described herein, and claims may be presented in this or a later application to any novel and non-obvious combination of these elements.

What is claimed is:

1. A method for preparing a population of antibodies wherein over 65% of the population are active antibodies, comprising:
    (a) loading a sample comprising a mixture of antibodies to a pre-equilibrated cation exchange column, then optionally washing the column with a wash buffer, and eluting antibodies bound to the column with an elution buffer, thereby removing host cell proteins (HCPs) and antibody isoforms from the sample, wherein the sample of step (a) has a conductivity of 5 to 7 mS/cm;
    (b) loading a sample prepared by mixing salt with the eluate of step (a) to a hydrophobic interaction column (HIC), and eluting the antibodies bound to the column with an elution buffer, thereby removing the host cell proteins (HCPs) from the eluate of step (a); and
    (c) loading the eluate of step (b) to an anion exchange column and collecting the flow-through.

2. The method according to claim 1, wherein the sample of step (a) is prepared by adjusting the pH of a culture supernatant to be in a range from pH 4 to 6 in order to remove precipitates.

3. The method according to claim 1, wherein the antibody has an isoelectric point of 8 to 10.

4. The method according to claim 1, wherein the antibody is Trastuzumab.

5. The method according to claim 1, wherein the eluate of step (a) comprises 65 to 80% active antibodies, 15 to 30% acidic antibody isoforms, and 5 to 20% basic antibody isoforms.

6. The method according to claim 1, wherein the antibody isoform of step (a) is an acidic antibody isoform.

7. The method according to claim 6, wherein the cation exchange column of step (a) comprises a cross-linked agarose resin having a —OCH$_2$COO— functional group.

8. The method according to claim 1, wherein the step (a) comprises:
   (i) loading the sample to the cation exchange column pre-equilibrated with an equilibration buffer comprising 20 to 30 mM sodium acetate (pH 4.5 to 5.5) and 35 to 45 mM sodium chloride;
   (ii) washing the column with a buffer comprising 20 to 30 mM sodium acetate (pH 4.5 to 5.5) and 35 to 45 mM sodium chloride;
   (iii) washing the column with a buffer comprising 20 to 30 mM Tris-hydrogen chloride (Tris-HCl) (pH 7.0 to 7.5);
   (iv) washing the column with a buffer comprising 20 to 30 mM Tris-hydrogen chloride (pH 7.0 to 7.5) and 20 to 30 mM sodium chloride;
   (v) washing the column with a buffer comprising 20 to 30 mM Tris-hydrogen chloride (pH 7.0 to 7.5); and
   (vi) eluting antibodies from the column with an elution buffer comprising 20 to 30 mM Tris-hydrogen chloride (pH 7.0 to 7.5) and 80 to 100 mM sodium chloride.

9. The method according to claim 1, wherein the antibody isoform of step (a) is an acidic antibody isoform and a basic antibody isoform.

10. The method according to claim 9, wherein the cation exchange column of step (a) comprises a methacrylate based polymer resin having a COO— functional group.

11. The method according to claim 10, wherein the step (a) comprises:
   (i) loading the sample to the cation exchange column pre-equilibrated with an equilibration buffer comprising 20 to 30 mM sodium acetate (pH 4.5 to 5.5) and 35 to 45 mM sodium chloride (NaCl);
   (ii) washing the column with a buffer comprising 20 to 30 mM sodium acetate (pH 4.5 to 5.5) and 35 to 45 mM sodium chloride;
   (iii) washing the column with a buffer comprising 25 to 35 mM sodium acetate (pH 5.5 to 6.5);
   (iv) washing the column with a buffer comprising 25 to 35 mM sodium acetate (pH 5.5 to 6.5) and 45 to 55 mM sodium chloride;
   (v) washing the column with a buffer comprising 25 to 35 mM sodium acetate (pH 5.5 to 6.5); and
   (vi) eluting antibodies from the column with an elution buffer comprising 25 to 35 mM sodium acetate and 70 to 90 mM sodium chloride.

12. The method according to claim 1, wherein the antibodies bound to the column of step (b) are eluted with a linear gradient in salt component of the elution buffer.

13. The method according to claim 12, wherein the step (b) comprises
   (i) loading a sample prepared by adjusting the citrate concentration of the eluate of step (a) to be the same as in an equilibration buffer comprising 25 to 35 mM acetate (pH 5.5 to 6.5) and 0.3 to 1.0 M sodium citrate, to hydrophobic interaction column (HIC) which is pre-equilibrated with the equilibration buffer; and
   (ii) eluting the antibodies with an elution buffer comprising 25 to 35 mM acetate (pH 5.5 to 6.5) in a linear gradient.

14. The method according to claim 1, wherein the hydrophobic interaction column of step (b) comprises a cross-linked agarose resin having a phenyl functional group.

15. The method according to claim 1, wherein the anion exchange column is equilibrated with an equilibration buffer in a range from pH 7.0 to 8.0, before loading.

16. The method according to claim 15, wherein the equilibration buffer comprises Tris-HCl (pH 7.0 to 8.0).

17. The method according to claim 1, wherein the anion exchange column of step (c) comprises a cross-linked agarose resin having a quaternary amine functional group.

18. The method according to claim 1, wherein the flow-through of the anion exchange column obtained from step (c) has a host cell protein (HCP) concentration of 0.001 to 5 ppm.

* * * * *